(12) United States Patent
Primavera et al.

(10) Patent No.: US 8,012,161 B2
(45) Date of Patent: Sep. 6, 2011

(54) SURGICAL SUTURING APPARATUS WITH MEASUREMENT STRUCTURE

(75) Inventors: Michael Primavera, Milford, CT (US); Kevin Clair, Easton, CT (US)

(73) Assignee: Tyco Healthcare Group LP, Norwalk, CT (US)

(*) Notice: Subject to any disclaimer, the term of this patent is extended or adjusted under 35 U.S.C. 154(b) by 94 days.

(21) Appl. No.: 12/413,924

(22) Filed: Mar. 30, 2009

(65) Prior Publication Data
US 2009/0248046 A1    Oct. 1, 2009

Related U.S. Application Data

(62) Division of application No. 10/529,567, filed as application No. PCT/US03/31640 on Oct. 6, 2003, now abandoned.

(60) Provisional application No. 60/416,058, filed on Oct. 4, 2002.

(51) Int. Cl.
*A61B 17/04* (2006.01)

(52) U.S. Cl. .......................................... 606/147

(58) Field of Classification Search .......... 606/144, 606/147–148
See application file for complete search history.

(56) References Cited

U.S. PATENT DOCUMENTS

| | | | |
|---|---|---|---|
| 3,079,606 A | 1/1963 | Bobrov et al. | |
| 3,317,105 A | 5/1967 | Astafjiev et al. | |
| 3,490,675 A | 3/1970 | Green et al. | |
| 3,499,591 A | 3/1970 | Green | |
| 4,244,370 A * | 1/1981 | Furlow et al. | 606/148 |
| 4,290,542 A | 9/1981 | Fedotov et al. | |
| D272,851 S | 2/1984 | Green et al. | |
| 4,491,133 A | 1/1985 | Menges et al. | |
| D278,080 S | 3/1985 | Green et al. | |
| D284,698 S | 7/1986 | Green | |
| 4,633,874 A | 1/1987 | Chow et al. | |
| 4,784,137 A | 11/1988 | Kulik et al. | |
| 5,010,892 A | 4/1991 | Colvin et al. | |
| 5,040,715 A | 8/1991 | Green et al. | |
| 5,083,695 A | 1/1992 | Foslien et al. | |
| 5,122,146 A | 6/1992 | Chapman | |
| 5,144,961 A * | 9/1992 | Chen et al. | 128/898 |
| 5,237,985 A | 8/1993 | Hodgson et al. | |
| 5,263,629 A | 11/1993 | Trumbull et al. | |

(Continued)

FOREIGN PATENT DOCUMENTS
DE            9317488       1/1994
(Continued)

OTHER PUBLICATIONS

European Search Report (EP 06 01 1963).

*Primary Examiner* — Darwin P Erezo
*Assistant Examiner* — Son Dang (57) ABSTRACT

There is disclosed suture manipulating instrumentation having measuring structure to determine the length of suture during a given point in a surgery. The instrument is preferably a surgical suturing instrument capable of manipulating a suture carrying needle at the distal end. The measuring structure in the form of a scale is provided on the suturing instrument at a location remote from the distal end. The length of suture can easily be determined with the use of the scale at any point during a surgery. There is also disclosed a kit for providing the suture measuring structure on other suture manipulating instruments, as well as, methods of using suture manipulating instrumentation having the disclosed measuring structure.

13 Claims, 9 Drawing Sheets

U.S. PATENT DOCUMENTS

| | | | |
|---|---|---|---|
| 5,320,629 A * | 6/1994 | Noda et al. | 606/139 |
| 5,478,344 A * | 12/1995 | Stone et al. | 606/144 |
| 5,562,703 A | 10/1996 | Desai | |
| 5,665,093 A * | 9/1997 | Atkins et al. | 606/108 |
| 5,762,256 A | 6/1998 | Mastri et al. | |
| 5,782,396 A | 7/1998 | Mastri et al. | |
| 5,865,724 A * | 2/1999 | Palmer et al. | 600/104 |
| 5,871,488 A | 2/1999 | Tovey et al. | |
| 6,032,849 A | 3/2000 | Mastri et al. | |
| 6,033,359 A | 3/2000 | Doi | |
| 6,109,500 A | 8/2000 | Alli et al. | |

FOREIGN PATENT DOCUMENTS

| | | | |
|---|---|---|---|
| EP | 0179623 | A2 | 4/1986 |
| EP | 0491537 | B1 | 6/1992 |

* cited by examiner

SURGICAL SUTURING APPARATUS WITH MEASUREMENT STRUCTURE

CROSS REFERENCE TO RELATED APPLICATION

This is a Divisional Application of U.S. patent application Ser. No. 10/529,567, filed Mar. 28, 2005, which is a National Stage Application of PCT/US03/31640, filed Oct. 6, 2003, under 35. U.S.C. §371(a), which claims priority to, and the benefit of, U.S. Provisional Patent Application Ser. No. 60/416,058, filed Oct. 4, 2002, entitled "Surgical Suturing Apparatus With Measurement Structure", now abandoned, the disclosures of which are hereby incorporated by reference in their entirety.

BACKGROUND

1. Technical Field

The present disclosure relates generally to surgical instrumentation and, more particularly, to surgical instrumentation having measuring apparatus for use in endoscopic or laparoscopic surgical procedures.

2. Description of Related Art

Endoscopic procedures are typically performed through an elongated cannula structure having a relatively small diameter with a proximal and distal end. In laparoscopic surgery an incision is made in the abdominal wall and the distal end of the cannula is passed through the tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

Many surgical procedures call for suturing tissue, a procedure traditionally accomplished by hand, or by passing a needle between forceps. Laparoscopic suturing presents a particularly challenging task, because it must be accomplished using instrumentation extended through a port that typically has an internal diameter that averages between five and twelve millimeters. Instruments for facilitating laparoscopic suturing are disclosed in U.S. Pat. No. 5,478,344, issued Dec. 26, 1995, to Stone et al., which is incorporated herein in its entirety by reference. The Stone et al. patent discloses in certain embodiments, a surgical suturing apparatus capable of passing control of a surgical needle, having a length of suture attached thereto, back and forth between its jaws to repeatedly pass the surgical needle and suture through tissue to suture tissue. In addition, it discloses methods of using the apparatus to suture tissue.

Other laparoscopic suturing instruments are also available in the marketplace. For example, U.S. Pat. No. 5,690,653, issued Nov. 25, 1997, to Richardson et al. discloses in certain embodiments a suturing device that includes an elongated tubular shaft having a needle disposed at the distal end. The needle is attached to a suture and is passed between one or more relatively movable jaws, as well as a method of using the device.

However, while the above-mentioned devices are valuable for laparoscopic suturing, none of the above-mentioned devices includes structure or discloses a method that facilitates measurement of the length of suture material while the device is in the body cavity. Therefore, a need exists for a suturing apparatus that maintains the advantages of laparoscopic suturing and incorporates a suture material measurement structure.

SUMMARY

Various measuring structures are provided for use with a number of different laparoscopic surgical instruments. The measuring structures are disposed on the apparatus for determining the length of a suture or determining the amount of suture material remaining when using the apparatus. Preferably, the measuring structure is an integral part of the laparoscopic instrument and is disposed at the distal end of the instrument for accurate measurement of the suture. Alternatively, the measuring structure is included in a kit that can be used with a number of different laparoscopic instruments. In either embodiment, the measuring structure has a number of graduations showing the selected units of measure. Further still, the measuring structure can be positioned such that the graduations are only visible from one vantage point. However, in a preferred embodiment, the measuring structure will be disposed so that it covers the outer perimeter of the surgical instrument substantially in its entirety. In this embodiment, the graduations of the measuring structure will be visible to the surgeon from most any vantage point enabling the surgeon to obtain a measurement without undue manipulation of the laparoscopic instrument.

Specifically a surgical instrument for manipulating a suture is disclosed including an elongate member having a distal end configured to manipulate a suture and a scale on at least a part of the elongate member and adjacent the distal end. The scale has at least one graduation and preferably a plurality of graduations to measure suture lengths. A predetermined point is identified on the elongate member such that the scale indicates the distance from the predetermined point to the at least one graduation. Preferably, the elongate member includes at least one jaw and the predetermined point is disposed on the the jaw. The jaw is configured to retain a needle carrying a suture and, alternatively, the predetermined point is located on the needle.

The surgical instrument is preferably a suturing apparatus and, predetermined point is located at the point of connection between the suture and the needle. The point of connection can be at one end of the needle, but preferably is located between the ends of the needle, especially with a double pointed needle.

The surgical instrument has at least one jaw is movable relative to the elongate member such that the distance from the predetermined point and the scale is calibrated with the at least movable jaw in a predetermined position. In a preferred embodiment of the surgical instrument the elongate member includes two movable jaws which are configured to repeatedly pass control of a needle carrying a suture therebetween and through tissue to form stitches.

The scale is provided to measure the remaining amount of suture after suturing and includes a plurality of graduations. Preferably, the scale is provided on a material affixed to the elongate member such as a shrink wrap affixed to the elongate member. Alternatively, the scale can be located on at least one longitudinally extending strip of material or etched into the elongate member. Preferably, the graduations indicate the distance in centimeters.

There is also disclosed a kit to assist manipulation of a suture with an elongate instrument including a scale configured to be attached to the distal end of a suture manipulating instrument and a template to calibrate the position of the scale relative the predetermined point on the distal end of the instrument. Preferably, the scale is provided on a shrink wrap material.

There is further disclosed a method of manipulating a suture by providing an elongate suture manipulating instrument configured to hold a first end of a suture at a predetermined point on a distal end of the instrument and a scale having at least one graduation provided on the instrument at a location remote from the distal end. During surgery a second end of the suture is grasped with a separate device and drawn along the instrument adjacent the scale so that a second end of the suture is adjacent the graduations on the scale to measure the length of suture. The drawing of the suture can be performed while the suture is being passed through tissue or after the suture is passed through tissue.

These together with other advantages will become apparent from the details of construction and operation as more fully hereinafter described.

BRIEF DESCRIPTION OF THE DRAWINGS

Various embodiments are disclosed herein with reference to the drawings wherein.

PIG. 1 is a perspective view of the distal end of a surgical suturing apparatus in accordance with an embodiment of the present disclosure, showing a measuring structure.

DETAILED DESCRIPTION OF PREFERRED EMBODIMENTS

The embodiments disclosed herein below relate to surgical instruments for manipulating a suture and having measuring structure to measure a length of suture at any time during a surgery.

FIGS. 1-7, show an embodiment of a suturing apparatus in accordance with an embodiment of the present disclosure. Suturing apparatus, generally indicated by reference numeral 10, has an elongated tubular housing or body portion 12, and two movable jaws (or jaw elements) 14 and 16. A needle 18 is releasably retained in one of jaws 14 and 16 at the distal end of suturing apparatus 10. Suturing apparatus 10 is configured to pass needle 18 back and forth between jaws 14 and 16. A length of suture 20 is connected to needle 18 such that passing needle 18 back and forth between tissue passes suture 20 through the tissue to form stitches. A measuring structure 90 is disposed on the distal portion of tubular housing 12 to measure the length of suture 20. As is conventional, the term "distal" refers to that direction further from the user while the term "proximal" refers to that direction closer to the user.

Figure 2:
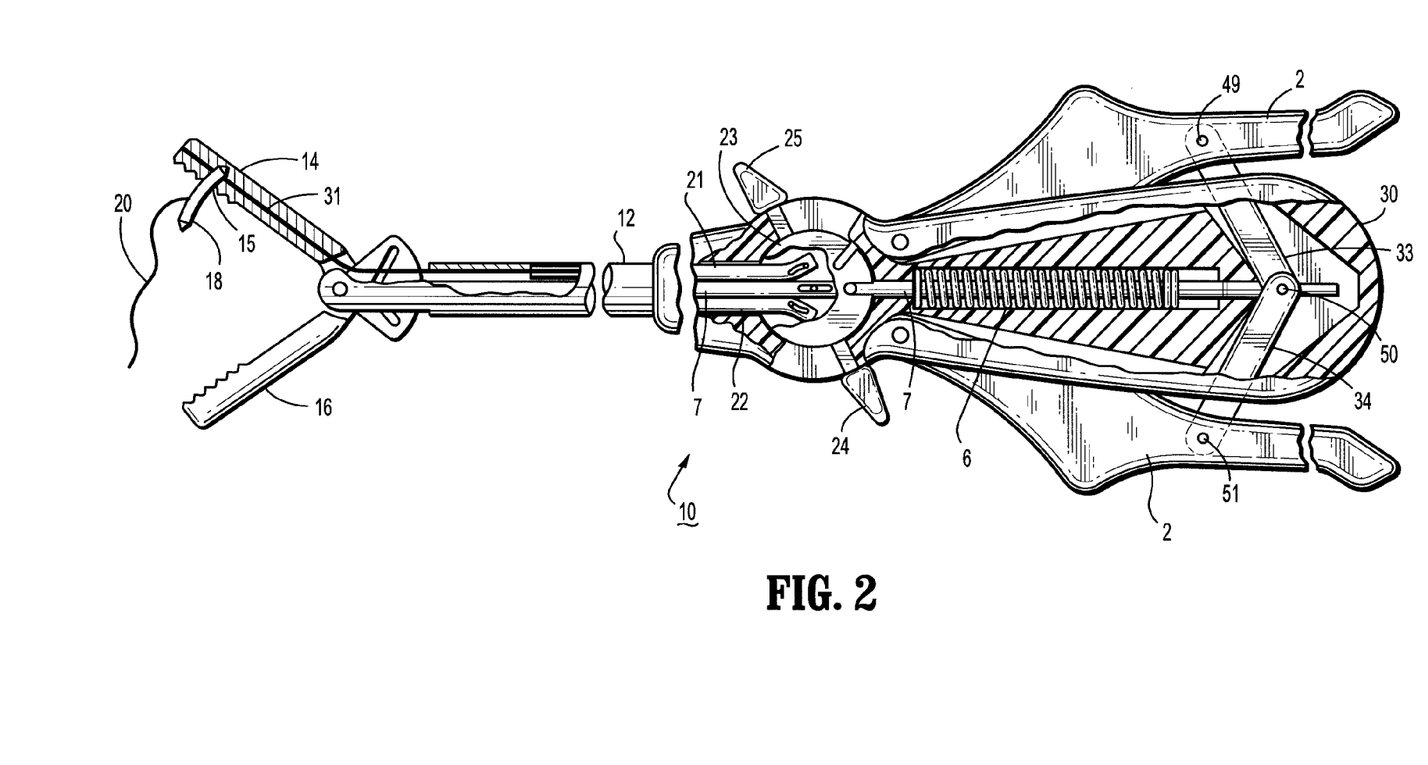
FIG. 2 is a side plan view, partially shown in section, of the suturing apparatus in accordance with the embodiment of FIG. 1.
Figure 3:
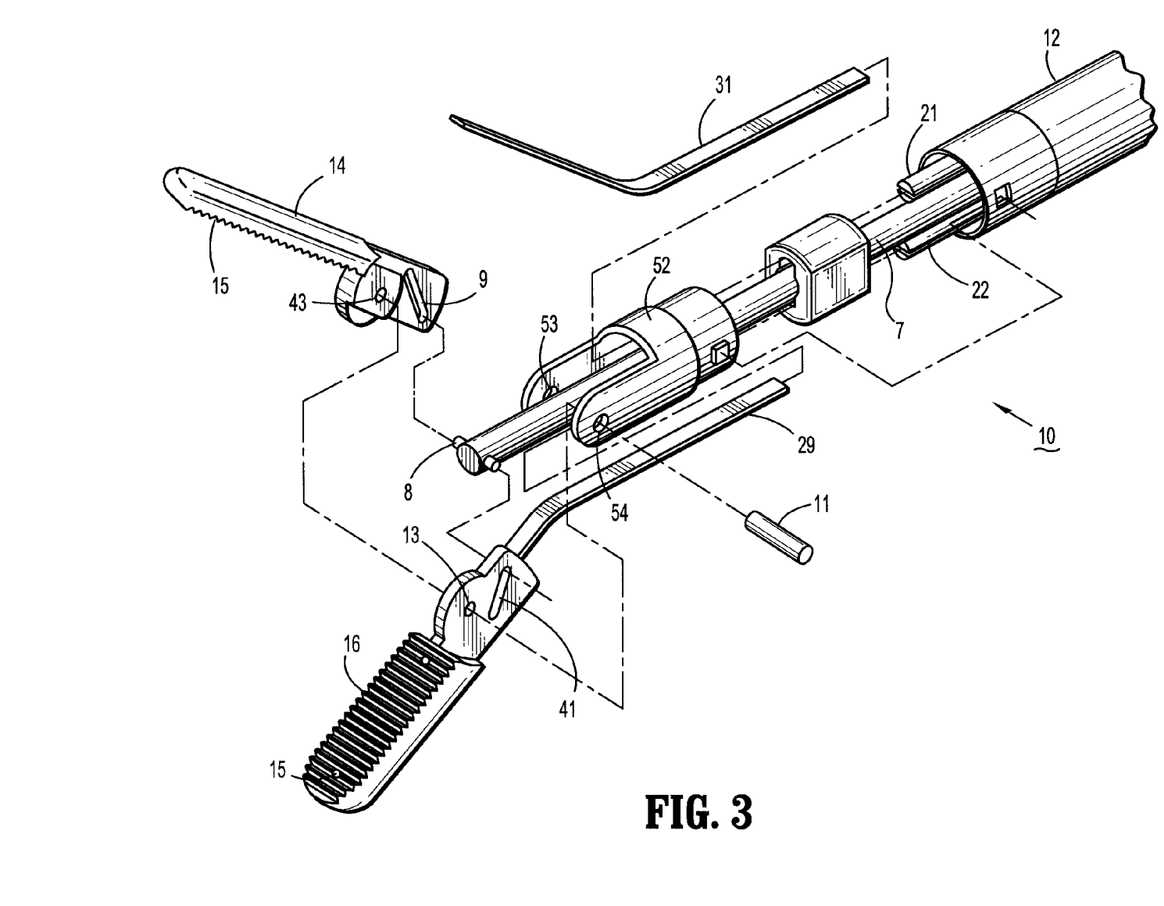
FIG. 3 is a exploded perspective view of the distal end of a surgical suturing apparatus in accordance with the embodiments of FIGS. 1 and 2.

Referring to FIGS. 2 and 3, there is shown suturing apparatus 10 in greater detail. Suturing apparatus 10 is described in certain embodiments of U.S. Pat. No. 5,690,653, the disclosure of which is hereby incorporated by reference herein. Suturing apparatus 10 has a handle housing 30 with a two-armed handle 2, elongated tubular housing 12, and two jaws 14 and 16. Handle 2 is used to control the opening and closing of jaws 14 and 16. Handles 2 are connected to a rod 7 by a pair of links 33 and 34 and pins 49,50 and 51. Center rod 7 is spring biased distally by spring 6. Spring 6 fits around center rod 7 and rests in a channel of housing 30. When the handles 2 are squeezed, center rod 7 moves backward (proximally), causing spring 6 to be compressed. Referring to FIG 3., the distal end of center rod 7 has a pin 8 which rides in a cam slots 9 and 41 in each of the jaws 14 and 16. Jaws 14 and 16 are pivotally connected to each other by pin 11 extending through holes 43 and 13 and through holes 53 and 54 of support 52. When center rod 7 is pulled proximally through actuation of the handles 2, pin 8 is also pulled proximally in cam slots 9 and 41, camming jaws 14 and 16 closed.

Each jaw 14 and 16 is adapted to receive needle 18 in recess 15. When jaws 14 and 16 are closed needle 18 sits in recesses 15 in both jaws 14 and 16. When jaws 14 and 16 are opened, needle 18 is retained in one or the other recesses 15 depending on which blade 31 or 29 intersects needle 18 through recess 15. Blade 31 cooperating with upper jaw 14 extends into recess 15 to secure needle 18. Alternatively, blade 29 may intersect needle 18 through recess 15, securing needle 18 in jaw 16. The movement of blades 31 and 29 to engage needle 18 will now be described.

On either side of center rod 7 are side rods 21 and 22 which sit inside tubular housing 12 and are connected at their proximal ends to a wheel 23 movably housed inside handle housing 30. Wheel 23 has two arms 24 and 25 projecting from either side that allow the operator of the apparatus to turn wheel 23. To transfer needle 18 from jaw 14 to jaw 16, the jaws are closed and wheel 23 is rotated by turning side arm 25 clockwise so that side rod 21 is pulled proximally and side rod 22 is pushed distally. Side rods 21 and 22 are connected to blades 31 and 29, respectively. Therefore, when side rod 22 is pushed distally, blade 29 is pushed distallly and engages needle 18 by extending into recess 15 to secure needle 18 in jaw 16. While blade 29 is in a distal position, blade 31 is in a retracted or proximal position, as each blade is connected to wheel 23 through a respective rod. Thus blade 31 docs not contact needle 18, thereby allowing release of the needle 18 from jaw 14. Similarly, side arm 24 may be turned counterclockwise, sliding side rod 21 and blade 31 distally and side arm 25 and blade 29 proximally, thereby securing needle in jaw 14 and allowing release of needle 18 from jaw 16.

Referring to FIGS. 1 and 4-7 measuring structure 90 has a scale 100 preferably disposed along a portion of tubular housing 12 such that scale 100 is adjacent to the distal end and extends longitudinally along tubular housing 12. Scale 100 has a longitudinal axis 101 that extends in the same direction as the longitudinal axis of body portion 120. A plurality of graduations 110 are disposed on scale 100 and are uniformly spaced apart along longitudinal axis 101 of scale 100. Graduations 110 indicate the distance from a predetermined point on the distal end of suturing apparatus 10. Preferably, the predetermined point is the point of connection between suture 20 and needle 18 to give an accurate measurement of the remaining usable length of suture 20. Since at least one of jaws 14 and 16 are movable, scale 100 must be calibrated with the jaw holding needle 18 in a predetermined position. This predetermined position may be fully open, fully closed or some predetermined position in between. Otherwise, movement of the jaw holding needle 18 will affect the measurement reading.

Graduations 110 may be marked with Arabic numerals, Roman numerals, Greek letters, or other suitable symbols of indicia. Preferably, graduations 110 are marked with Arabic numerals so that the units of measure are readily ascertainable. Although graduations 110 are shown in centimeters, the actual units of measure may be changed to suit the user's needs without departing from the scope of the disclosure (e.g. inches, millimeters, decimeters, etc.).

Figure 1:
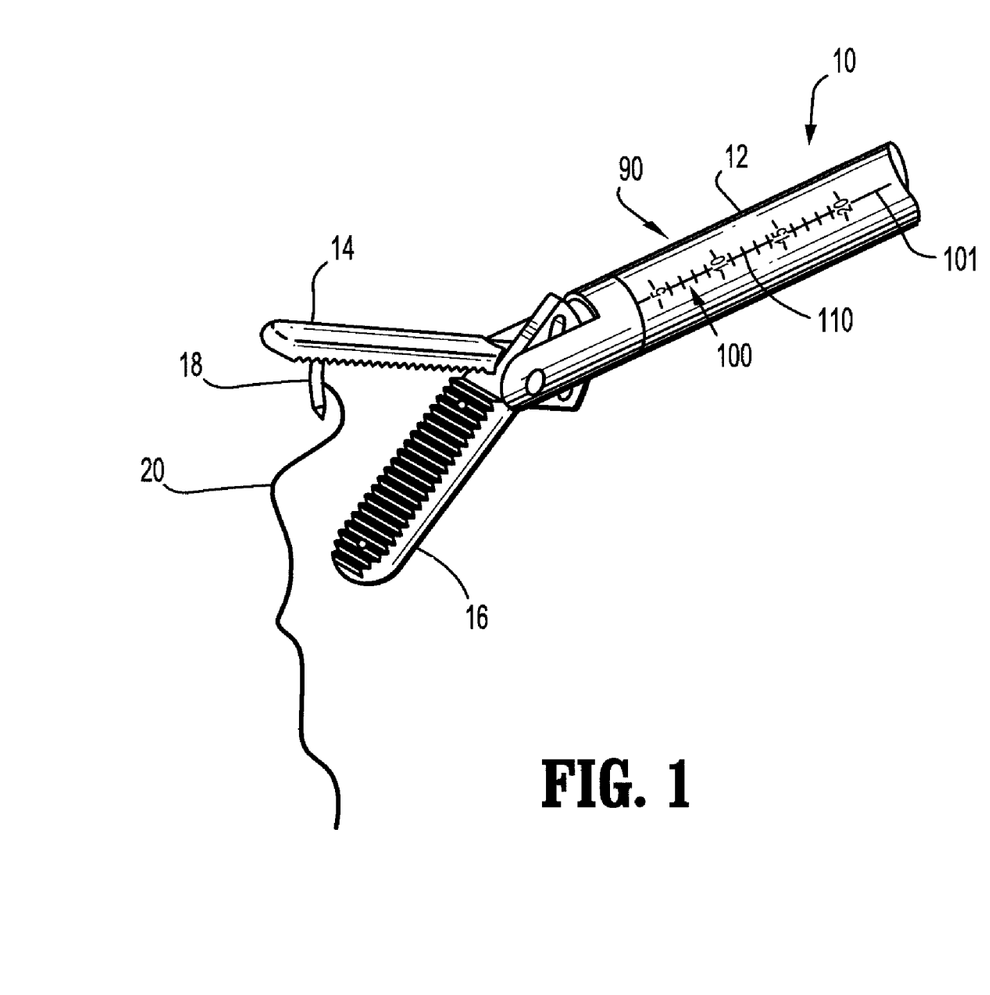
Figure 4:
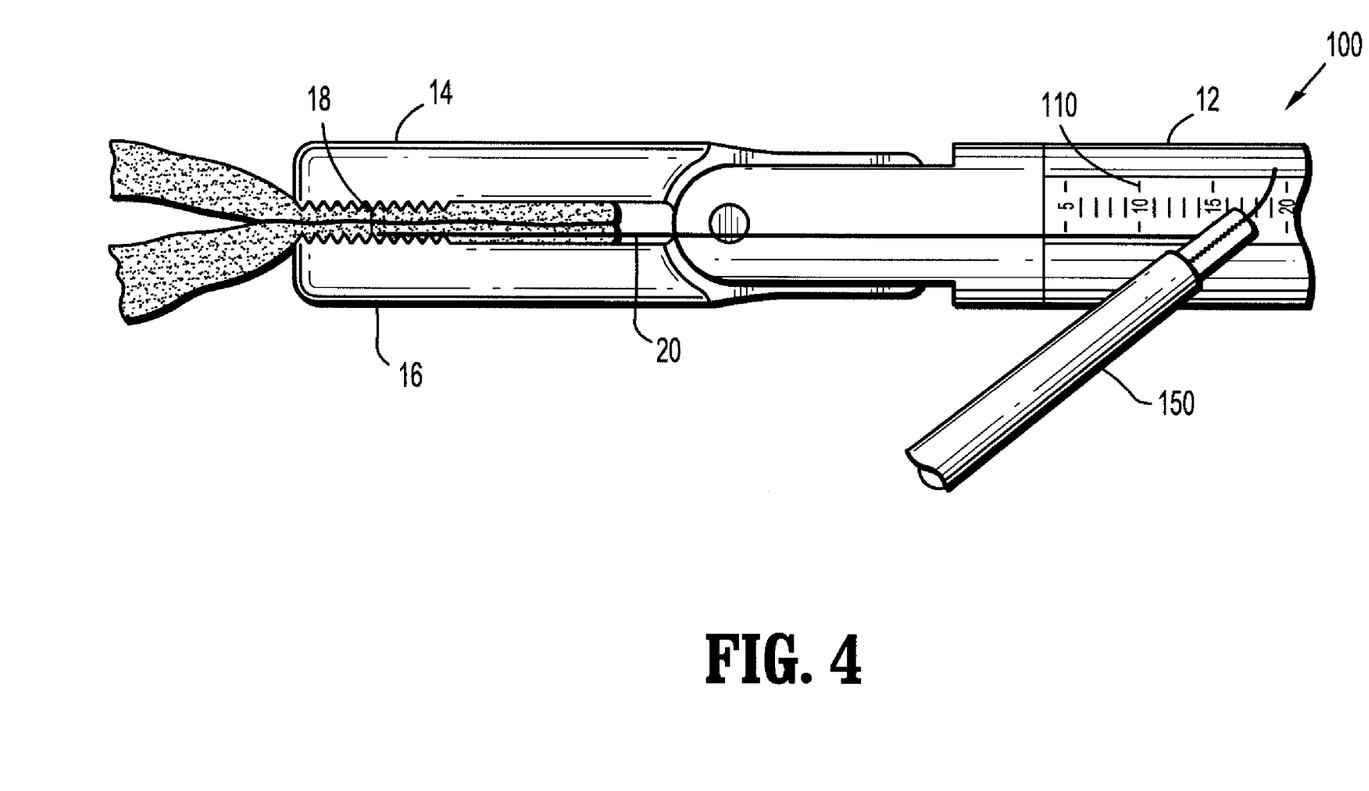
FIG. 4 is a side view of the distal end of the suturing apparatus in accordance with the embodiment of FIGS. 1-3, showing a grasping instrument holding the suture along the measuring structure.

As shown in FIGS. 1 and 4, graduations 110 on scale 100 are generally in the same viewing plane as needle 18. Placing needle 18 and graduations 110 in the same viewing plane allows the surgeon using suturing apparatus 10 to observe scale 100, needle 18 and a suture 20 simultaneously. However, during endoscopic surgery, the surgeon's field of view is limited by the endoscope, and suture 20 may not lie in the field of view of the endoscope. It is preferred that graduations 110 be visible to the surgeon regardless of the physical orientation of the surgical instrument. Therefore, the lateral dimensions of scale 100 and graduations 110 are such that graduations 110 cover a large enough area on tubular housing 12 so that graduations 110 are visible to the surgeon regardless of the orientation of the surgical instrument. Scale 100 and graduations 110 may cover the full perimeter of body portion 12 or only a part thereof.

Extending scale 100 and graduations 110 along a greater portion of the surface of regular housing 12 does not alter the accuracy of the instrument since graduations 110 are still uniformly spaced apart, but allows graduations 110 to be visible in more than one plane of view. For example, graduations 110 may encompass approximately up to 90 degrees of the surface of tubular housing 12 as shown in FIG. 1. In addition, more than one scale may be disposed on a surgical instrument such as disposing a number of scales around the surface of tubular housing 12. When a number of scales are disposed in this fashion, the scales may be contiguous or may be transversely spaced apart. Preferably, graduations 110 will extend circumferentially about tubular housing 12 up to and including 360 degrees of the surface.

Scale 100 and graduations 110 are shown in the figures as being disposed on tubular surgical instruments for illustrative purposes only. It is within the scope of this disclosure for scale 100 and graduations 110 to be disposed on instruments that have regular or irregular polygonal shapes. With instruments that have regular or irregular polygonal shapes, graduations 110 may be disposed on one or more surfaces of the polygon, alternating surfaces of the polygon or all surfaces of the polygon depending on the particular instrument and its application.

Figure 5:
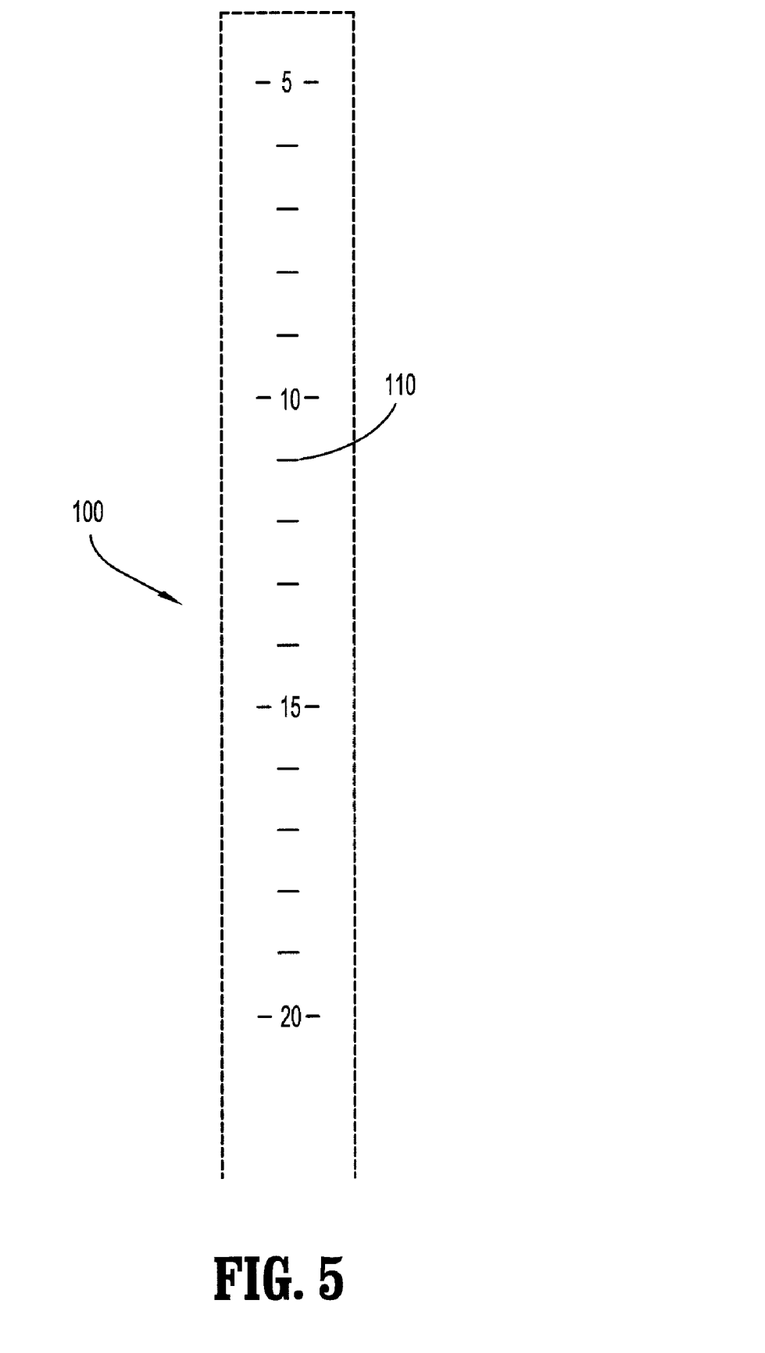
FIG. 5 is a plan view of a measuring structure in accordance with the embodiment of FIGS. 1-4.

A more detailed view of scale 100 with graduations 110 is shown in FIG. 5. Although scale 100 is shown having a range of 5-20 units, preferably centimeters, other units and ranges are entirely within the scope of the present disclosure. The selected range of scale 100 and units of graduations 110 are determined by the user's requirements. In the present example of 5-20 centimeters, scale 100 has an accuracy of +/−0.6 centimeters. In this figure, the scale 100 uses one (1) unit graduations commencing with the numeral five (5). It is within the scope of the disclosure that scale 100 could be designed to include graduations 110 representing less than one (1) unit (i.e. ½ unit) or units greater than one (1) unit (e.g. 1½, 2, or 5). The number of units represented by each graduation 110 is not limited to what is disclosed here, but is to be determined by the ultimate application of the scale 100. In addition, graduations 110 are illustrated in centimeters, the actual units of measure may be changed to suit the user's needs without departing from the scope of the disclosure (e.g. inches, millimeters, decimeters, etc.).

Figure 6:
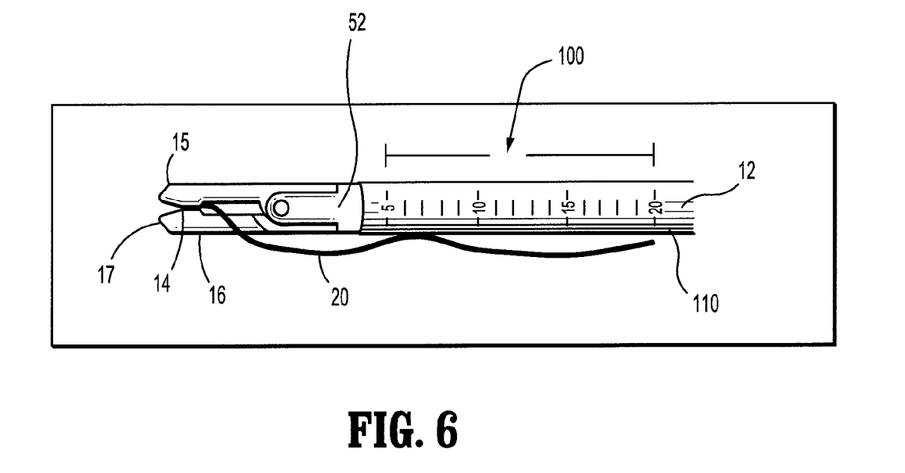
FIG. 6 is a side view of the distal end of the suturing apparatus in accordance with the embodiment of FIGS. 1-5, illustrating the measuring structure measuring a length of suture material.
Figure 7:
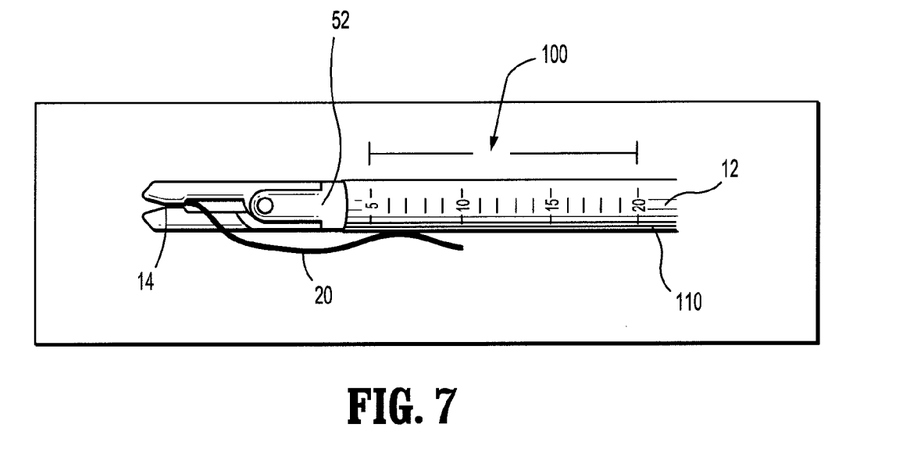
FIG. 7 is a side view of the distal end of the tubular housing in accordance with the embodiment of FIG. 1-6, illustrating the measuring structure measuring a different length of suture material.

FIGS. 6 and 7 depict the distal end of tubular housing 12 of suturing apparatus 10. Scale 100 is disposed adjacent and posterior to the jaw support 52. In FIG. 6, scale 100 shows that approximately twenty (20) centimeters of suture 20 are attached to needle 18. It should be noted that the figure is not to scale as it appears that the distance from the predetermined point to the first graduation is greater than 5 cm and that while suture 20 appears loose in FIGS. 6 and 7, in actuality suture 20 would be slightly tensioned or straightened as shown in FIG. 2 to give an accurate reading. Furthermore, it is necessary that suture 20 be drawn along a direct line from its point of connection with needle 18 to give an accurate measurement. Care should be taken that suture 20 not get caught on, or bend around the distal most ends 15 and 17 of jaws 14 and 16, respectively, as this would give an incorrect measurement indicating a smaller amount of suture 20 left than is actually the case.

FIG. 7 illustrates the situation in which one or more stitches have been sewn leaving approximately ten (10) centimeters of suture 20 available for use. The accuracy of scale 100 is +/−0.6 graduations, or in the present example +/−0.6 centimeters. The ability of the surgeon to discern the remaining length of suture 20 easily and readily enables the surgeon to predict the number of sutures that can be safely sewn before it is necessary to remove suturing apparatus 10 for reloading.

Although suturing apparatus 10 will be periodically removed for reloading, the addition of attached scale 100 permits the surgeon to minimize the number of reloading operations that must be performed clue to guess work involved in determining the amount of suture 20 remaining. This enables the surgeon to minimize the time of the procedure and optimize the quantity of suture material used. Scale 100 is envisioned to be incorporated into the structure of tubular housing 12 during the manufacturing process wherein graduations 110 would be etched, embossed or otherwise permanently part of tubular housing 12.

Alternately, scale 100 and graduations 110 could be supplied as part of a kit to allow the surgeon to select the units of measurement and the length of scale 100. Furthermore, supplying scale 100 in kit form allows existing owners of suturing apparatus 10 to take full advantage of this disclosure without the need to purchase new suturing apparatus 10. For example, the kit could include several scales 100 having different ranges of graduations, different units of measurement, or numerous combinations of the preceding depending on the demands of the marketplace. In one embodiment, each scale 100 that is supplied as part of a kit would has an adhesive backing for attachment to tubular housing 12 and that this adhesive backing would securely attach scale 100 to tubular housing 12 to alleviate any concerns about scale 100 becoming dislodged in the cavity during the endoscopic procedure.

The preferred method for attaching scale 100 is to place scale 100 on heat shrinkable tubing. During preparation for surgery, the heat shrinkable tubing would be placed over the distal end of the surgical instrument and moved towards the proximal end along the longitudinal axis of the instrument. Once the heat shrinkable tubing is properly positioned, a flameless heat source is applied uniformly to the heat shrinkable tubing. Once the heat shrinkable tubing has shrunk to its designed size, and conformed to the shape of the surgical instrument, the heat source is removed leaving the surgical instrument with a measuring apparatus properly positioned for use. Further still, the kit may include an assembly template or other calibration device to ensure that scale 100 is disposed along tubular housing 12 with the proper orientation and proper longitudinal positioning from the predetermined point. The tubular housing 12 and heat shrinkable tubing may include reference marks that are aligned by placing the heat shrinkable tubing on tubular housing 12. This is essential so that each suturing apparatus 10 will produce the same accurate measurements and ensure highly repeatable results for the surgeon.

Referring now to FIG. 4, the use of suturing apparatus 10 including scale 100 to suture tissue and measure the remaining amount of suture 20 will now be described. As noted above, scale 100 is disposed along the longitudinal axis of tubular housing 12 and posterior to jaws 14, 16 with suture 20 extending from a predetermined point which is preferably the connection point with needle 18. During laparoscopic suturing, the surgeon closes jaws 14, 16 about the tissue, forcing needle 18 and suture 20 to pierce the tissue and passes control of the needle 20 between jaws 14 and 16. Next, the surgeon then takes a grasping tool 150 and grabs the distal end of suture 20 with grasping tool 150. Using grasping tool 150, the surgeon holds suture 20 taut against the surface of scale 100 thereby allowing the surgeon to measure the length of suture 20. By holding suture 20 taut against scale 100, the surgeon is able to read the remaining length of suture 20 accurately. Again, care should be taken to ensure that suture 20 extends in a generally straight line from the predetermined point to scale 100 and does not become wrapped around the distal most ends of the jaws which would cause an inaccurate reading.

It should be noted that by measuring the remaining usable length of suture after a stitch, the surgeon can estimate the number of stitches that can be performed before having to reload a new needle and suture to a fairly certain degree of accuracy. This asset is not limited to endoscopic uses of measuring structure on suture manipulating instruments, but rather, may also find useful application in open surgery.

Alternatively, the surgeon may pass needle 18 through the tissue and move suturing apparatus 10 adjacent the tissue and then take the measurement. As noted above, the measurement is taken with suture 20 extending from a predetermined point and with at least one of jaws 14 and 16 in a predetermined position corresponding to the calibration of scale 100 on suturing apparatus 10.

Figure 8:
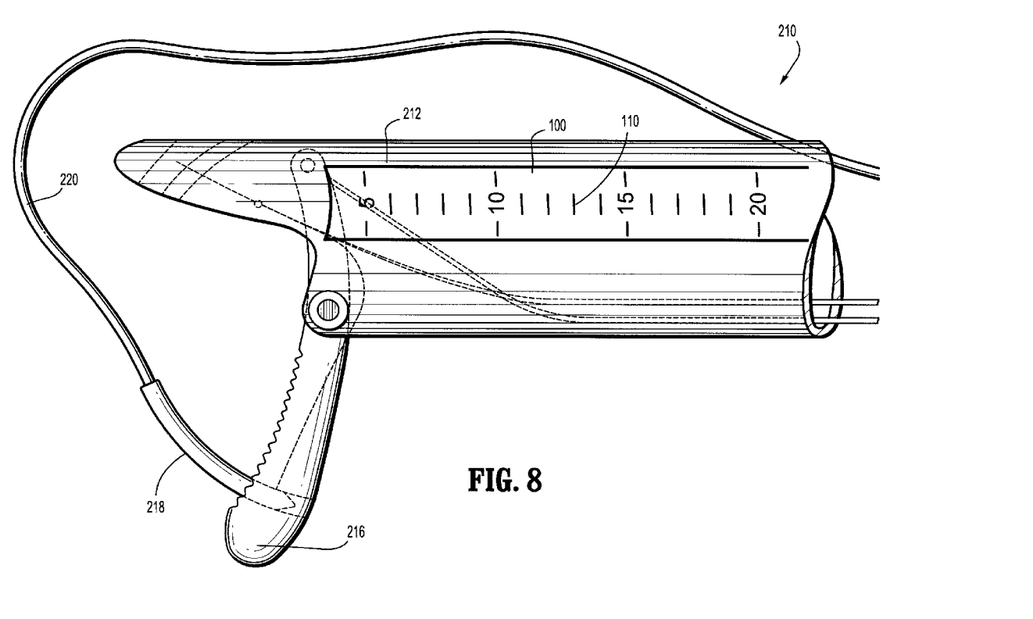
FIG. 8 is a perspective view of the distal end of a surgical suturing apparatus in accordance with a further embodiment of the present disclosure.

Turning to FIG. 8, the distal end of a surgical suturing apparatus in accordance with a further embodiment is illustrated. This particular surgical instrument 210 includes a tubular housing 212 with only one movable or pivotably hinged jaw 216 disposed at the distal end of tubular housing 212. A needle 218 is removably receivable by an aperture in jaw 216. A suture 220 is attached to the end of needle 218, which establishes the predetermined point for the measuring structure of this apparatus, and the remaining length of suture 220 is disposed along the longitudinal axis of tubular housing 212. Scale 100 is disposed near the distal end of tubular housing 212 and preferably covers the entire outer perimeter of tubular housing 212 so that graduations 110 are visible to the surgeon regardless of the orientation of surgical suturing apparatus 210. Scale 100 is calibrated to read accurately with jaw 216 in the predetermined position, i.e., fully open, fully closed or some predetermined position in between.

Figure 9:
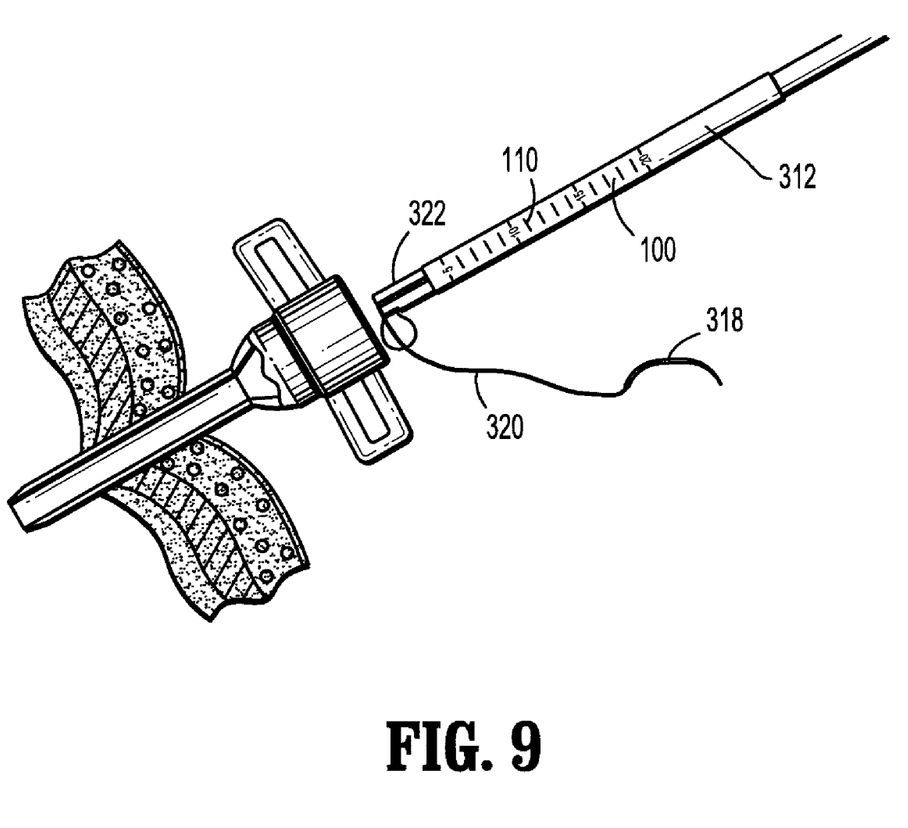
FIG. 9 is a perspective view of the distal end of a surgical apparatus in accordance with another embodiment of the present disclosure.

In FIG. 9, a surgical suturing apparatus in accordance with yet another embodiment is illustrated. As in previous embodiments, the surgical suturing apparatus 310 has a scale 100 disposed near the distal end of a tubular housing 312. A suture 320 extends from the most distal end of tubular housing 312 with a needle 318 at the distal end of suture 320. Needle 318 and suture 320 are attached to a cartridge carrier 322 that is removably attached to tubular housing 312. It is preferred that scale 100 and graduations 110 are disposed such that graduations 110 encompass the entire outer perimeter of tubular housing 312 of surgical suturing apparatus 310.

Figure 10:
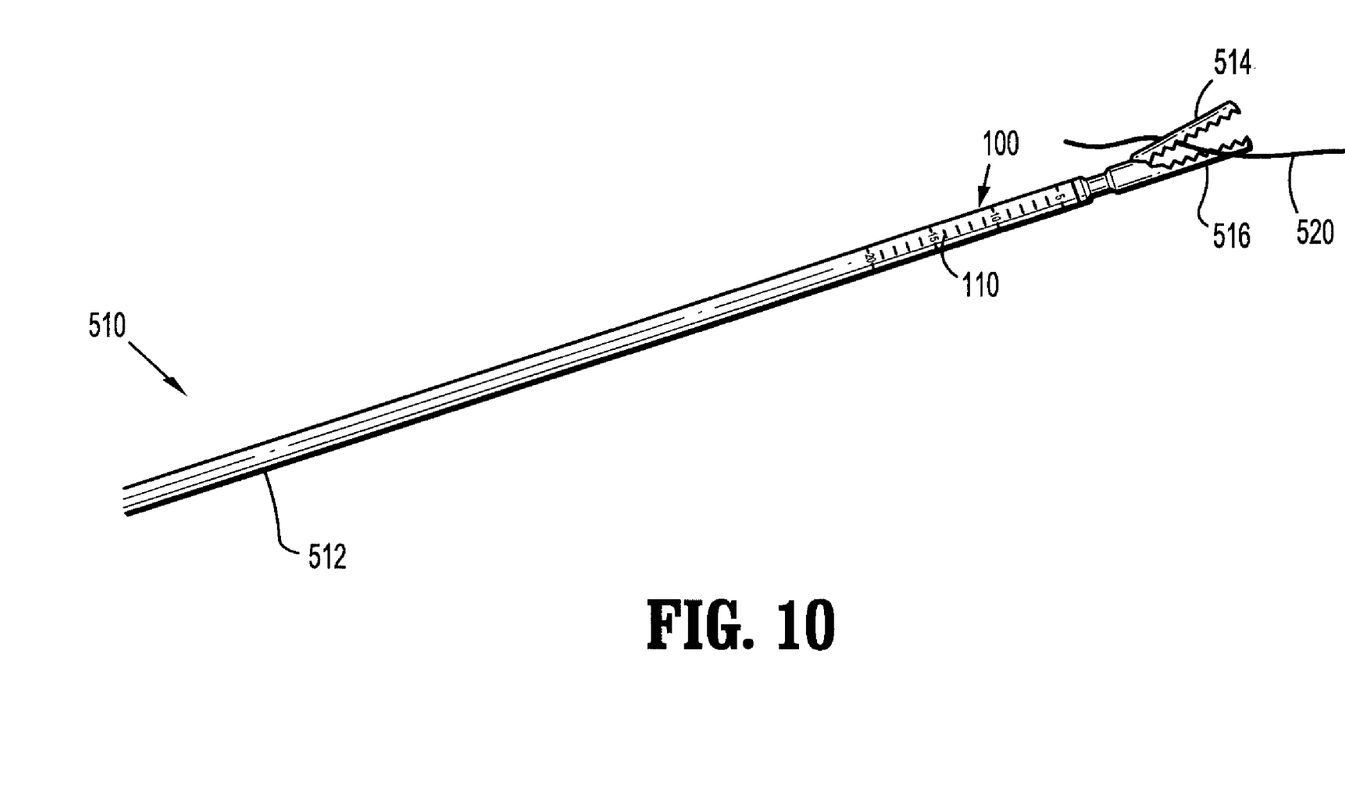
FIG. 10 is a perspective view of a surgical grasping instrument in accordance with another embodiment of the present disclosure.

Referring to FIG. 10, a surgical instrument in accordance with a further embodiment is shown. Similar to previous instruments, surgical instrument 510 is particularly arranged for laparoscopic or other minimally invasive surgery and it includes an elongate tubular housing 512. Surgical instrument 510 has a grasping tool 514 at the distal end of tubular housing 512. This instrument permits the surgeon to grasp a suture 520 and determine the length of the unused portion. Once again, scale 100 is disposed along the distal end of tubular housing 512 just posterior to grasping tool 514. Having scale 100 disposed in this location permits the surgeon to determine the length of suture 520 accurately by moving suture 520 with grasping tool 514 along the side of tubular housing 512 to measure the length of suture 520. It is preferred that scale 100 and graduations 110 cover the outer perimeter of tubular housing 512 so that the surgeon can view graduations 110 without having to reposition surgical instrument 510. The surgical instrument 510 may be used to manipulate a needle and suture or may be used in conjunction with a suturing apparatus.

It will be understood that various modifications may be made to the embodiments disclosed herein. For example, the unit may be color coded to indicate the range and units of measurement. When supplied as part of a kit, it is fully compatible with other laparoscopic surgical instruments such as scissors, knot-tying tools, and other tools. Further still, other methods for disposing measuring structures on surgical instruments such as shrink-wrapping may be employed. Therefore, the above description should not be construed as limiting, but merely as exemplifications of preferred embodiments. Those skilled in the art will envision other modifications within the scope and spirit of the claims appended hereto.

The foregoing is considered illustrative only of the principles of the measuring apparatus. Further, this is not intended to be limited to the exact structure, construction and operation shown and described.

What is claimed is:

1. A method for measuring a length of a suture during surgery, a suture comprising:
    providing an elongate suture manipulating instrument configured to hold a first end of a suture at a predetermined point on a distal end of the instrument and a scale having at least one graduation provided on the instrument at a location remote from the distal end;
    grasping a second end of the suture with a separate device; and
    drawing the suture along the instrument adjacent the scale so that a second end of the suture is adjacent the at least one graduation on the scale to measure the length of suture while the instrument is in the body cavity.

2. The method as recited in claim 1, wherein the step of drawing is performed while the suture is being passed through tissue.

3. The method as recited in claim 1, wherein the step of drawing is performed after the suture is passed through tissue.

4. The method as recited in claim 1, further comprising measuring the length of suture with the scale.

5. The method as recited in claim 4, further comprising aligning the suture adjacent the at least one graduation.

6. The method as recited in claim 5, further comprising determining the distance from the predetermined point to the at least one graduation.

7. The method as recited in claim 1, further comprising etching the scale into the elongate member.

8. The method as recited in claim 1, further comprising positioning the scale on a shrink wrap affixed to the elongate suture manipulating instrument.

9. The method as recited in claim 1, further comprising positioning the scale on at least one longitudinally extending strip of material affixed to the elongate suture manipulating instrument.

10. The method as recited in claim 1, further comprising calibrating the scale relative to the predetermined point.

11. The method as recited in claim 10, further comprising providing the scale with a plurality of graduations and calibrating each of the plurality of graduations to provide specific dimensional relationships between each of the plurality of graduations and the predetermined point.

12. The method as recited in claim 11, further comprising providing numerical indicia adjacent each graduation indicative of the distance from the predetermined point.

13. The method as recited in claim 12, further comprising labeling the numerical indicia in centimeters.

* * * * *